US00PP35663P2

(12) United States Plant Patent
Read

(10) Patent No.: US PP35,663 P2
(45) Date of Patent: Feb. 20, 2024

(54) ***GAILLARDIA* PLANT NAMED 'FANFARE SERENADE'**

(50) Latin Name: ***Gaillardia* x *grandiflora***
Varietal Denomination: Fanfare Serenade

(71) Applicant: Charles Richard Read, Bognor Regis (GB)

(72) Inventor: Charles Richard Read, Bognor Regis (GB)

( * ) Notice: Subject to any disclaimer, the term of this patent is extended or adjusted under 35 U.S.C. 154(b) by 0 days.

(21) Appl. No.: 18/182,337

(22) Filed: Mar. 11, 2023

(51) Int. Cl.
*A01H 5/02* (2018.01)
*A01H 6/14* (2018.01)

(52) U.S. Cl.
USPC ..... Plt./431
CPC ..... *A01H 6/14* (2018.05)

(58) Field of Classification Search
USPC ..... Plt./431, 263.1, 226
CPC ..... A01H 5/02
See application file for complete search history.

(56) References Cited

PUBLICATIONS https://lori.ru/40691442; Jul. 26, 2022; 1 page.*

* cited by examiner

*Primary Examiner* — Kent L Bell
(74) *Attorney, Agent, or Firm* — Weatherly IP Solutions, LLC; James M. Weatherly

(57) ABSTRACT

A new cultivar of *Gaillardia* plant named 'Fanfare Serenade' that is distinguishable by its compact and upright plant habit, large showy inflorescences composed of tubular ray florets arranged around a central disc composed of numerous small disc florets. When fully expanded, the tubular ray florets of 'Fanfare Serenade' are predominantly red in color with short bright yellow tips.

2 Drawing Sheets

Figure 1:
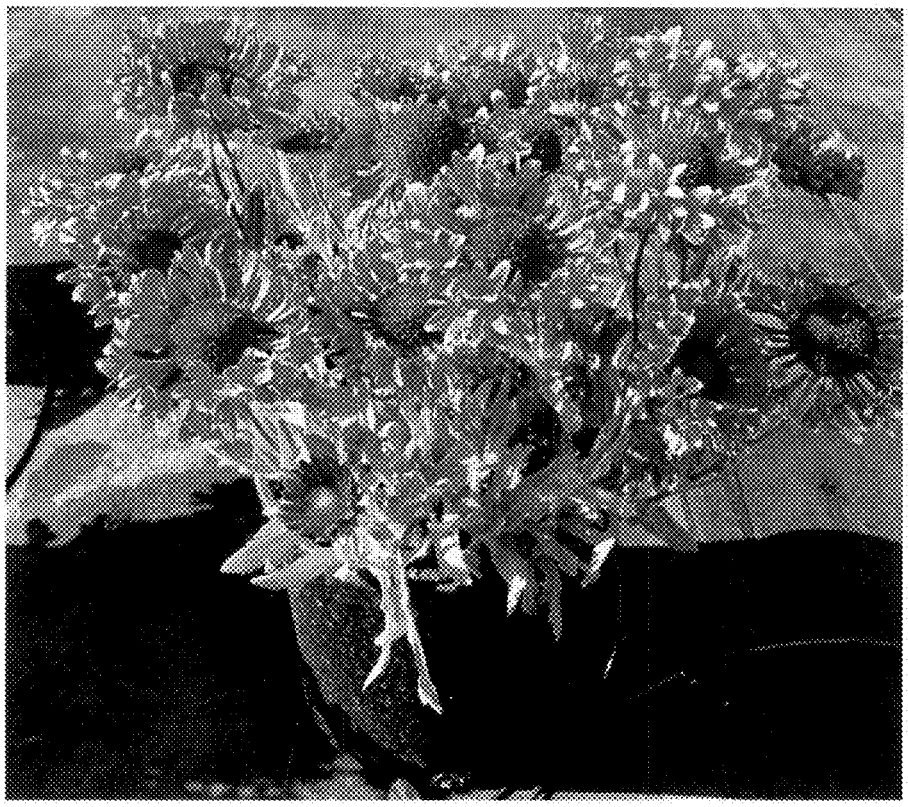

Genus and species: *Gaillardia* x *grandiflora*.
Variety denomination. 'Fanfare Serenade'.

BACKGROUND OF THE NEW PLANT

The present invention relates to a new and distinct cultivar of *Gaillardia*, commonly known as blanket flower, an herbaceous perennial that is grown for use as an ornamental landscape and container plant. The new invention is known botanically as *Gaillardia* x *grandiflora* and will be referred to hereinafter by the cultivar name 'Fanfare Serenade'. *Gaillardia* is in the family Compositae, under which the commonly referred to "flower" is actually the inflorescence, and is made up of showy ray florets and small disc florets.

'Fanfare Serenade' is the result of a controlled hybridization carried out as part of a long-term breeding programme commenced in 2012. The aims of the breeding program are to introduce strong-growing plants with combinations of new inflorescence colors and new ray floret shapes. The breeding program is carried out at the inventor's nursery in West Sussex, England. The inventor selected male and female parents from previously hybridized selections which are unreleased and unpatented. The female parent of 'Fanfare Serenade' is identified as *Gaillardia* seedling G1313-4. The male parent of 'Fanfare Serenade' is identified as *Gaillardia* seedling G1421-2.

The inventor selected 'Fanfare Serenade' in 2020 and first asexually reproduced 'Fanfare Serenade' in 2021 by rooting softwood cuttings in a greenhouse at the inventor's nursery in West Sussex, United Kingdom. Since that time, the inventor has determined that 'Fanfare Serenade' is stable and remains true-to-type in successive generations of asexual reproduction.

SUMMARY

The following traits have been repeatedly observed and represent the distinguishing characteristics of 'Fanfare Serenade'. These traits in combination distinguish 'Fanfare Serenade' from all other existing varieties of *Gaillardia* x *grandiflora* known to the inventor. 'Fanfare Serenade' has not been tested under all possible conditions and phenotypic differences may be observed with variations in environmental, climatic, and cultural conditions, without any variance in genotype.

1. 'Fanfare Serenade' exhibits a compact and upright plant habit.
2. 'Fanfare Serenade' bears large showy inflorescences composed of tubular ray florets arranged around a central disc composed of numerous small disc florets.
3. When fully expanded, the tubular ray florets of 'Fanfare Serenade' are bicolored, red and yellow.
4. The outer surface of the corolla tube of the ray florets of 'Fanfare Serenade' is dark red in color, and the inner surface of the tube is bright red in color.
5. The unfused portion of the ray florets of 'Fanfare Serenade' are red in color except for short yellow tips.
6. 'Fanfare Serenade' is 45 cm-50 cm in height and 40 cm in width after one year's growth from a rooted cutting.
7. 'Fanfare Serenade' is hardy at least to USDA Zone 6.

COMPARISON WITH PARENTAL LINES AND KNOWN VARIETY

Whereas the inflorescences of 'Fanfare Serenade' are comprised of fully tubular ray florets which are predominantly red in color with short bright yellow tips, the male parent, seedling G1421-2, bears semi-tubular ray florets which are orange in color, and the female parent, seedling G1313-4, bears flat ray florets which are red in color, with yellow apices. In addition, plants of 'Fanfare Serenade' bear larger and more numerous inflorescences and have a stronger growth habit than either of the parents.

The inventor considers that the closest variety of *Gaillardia* relative to 'Fanfare Serenade' is *Gaillardia* Plant Named 'Fanfare' (U.S. Plant Pat. No. 15,892). Both 'Fanfare' and 'Fanfare Serenade' bear bi-colored red and yellow tubular ray florets. However, the diameter of the inflorescence of 'Fanfare' is 60 mm-70 mm, whereas the inflorescence of 'Fanfare Serenade' is 80 mm in diameter. In addition, the corolla tube of 'Fanfare' is soft red in color with red veins, whereas the corolla tube of 'Fanfare Serenade' is dark red in color, with dark purple veins. Finally, the yellow tips of the ray florets of 'Fanfare' extend entirely over the free portion of the ray florets, whereas the yellow tips on the ray florets of 'Fanfare Serenade' are very short in comparison.

DESCRIPTION OF THE PHOTOGRAPHS

The accompanying color photographs illustrate the overall appearance of the new *Gaillardia* cultivar 'Fanfare Serenade' showing the colors as true as is reasonably possible to obtain in colored reproductions of this type. Colors in the photograph may differ from the color values cited in the detailed botanical description, which accurately describes the observed colors of the new variety 'Fanfare Serenade'.

The photograph labeled as FIG. 1 depicts a whole plant of 'Fanfare Serenade' which was growing out of doors in Santa Barbara, California. The illustrated plant has been grown for one year after transplanting a rooted cutting. The photograph was taken in the last week of May when the variety is first in full bloom.

Figure 2:
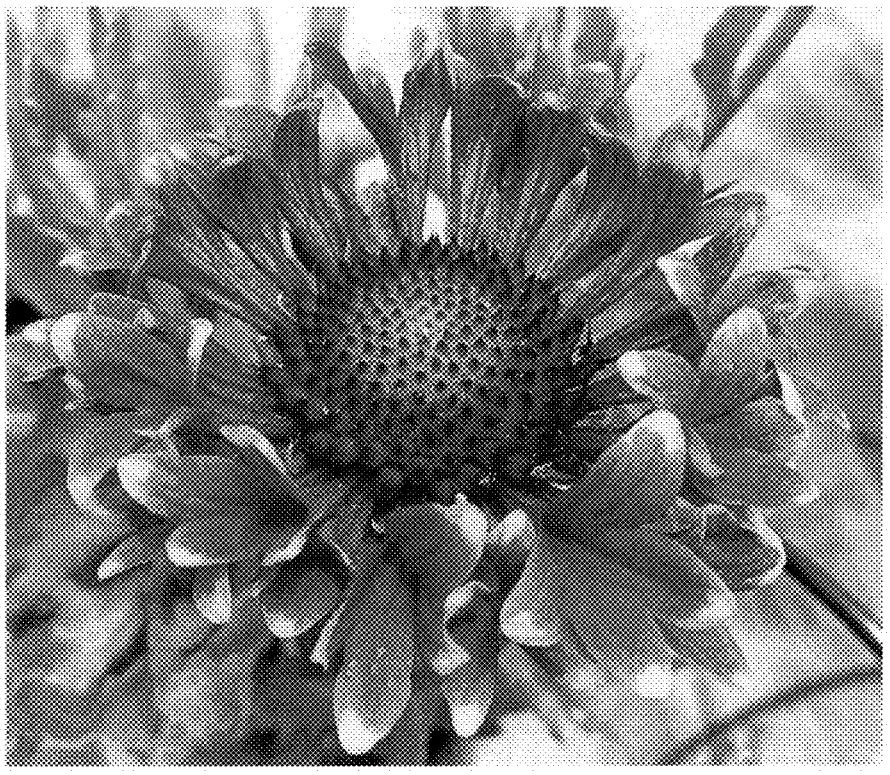

The photograph labeled as FIG. 2 depicts a fully expanded inflorescence of 'Fanfare Serenade'.

BOTANICAL DESCRIPTION OF THE PLANT

The following is a detailed botanical description of the new *Gaillardia* x *grandiflora* cultivar 'Fanfare Serenade'. Observations, measurements, values and comparisons were compiled in Santa Barbara, California from one-year-old plants growing in a 2-gallon container. The plant had been grown in an unheated greenhouse during the rooting stage and transferred to an open-air bed until flowering. Color determinations are made by reference to the 2007 edition of The Royal Horticultural Society Colour Chart from London, England, except where general color terms of ordinary significance are used.

Botanical classification:

*Genus.*—*Gaillardia.*

*Species.*—x *grandiflora.*

*Variety.*—'Fanfare Serenade'.

*Common name.*—Blanket flower.

*Parentage.*—*Gaillardia* x *grandiflora* 'Fanfare Serenade' was selected as seedling which resulted from the controlled cross of the following parent plants: Female parent: Proprietary *Gaillardia* seedling G1313-4. Male parent: Proprietary *Gaillardia* seedling G1421-2.

*Propagation method.*—Softwood cuttings.

*Rooting system.*—Fine and fibrous, color 156B.

*Vigor.*—Moderate vigor.

*Time to develop roots.*—14 to 20 days are needed for an initial cutting to develop roots.

*Temperature to develop roots.*—The recommended air temperature is 20°-21° Centigrade.

*Crop time.*—Approximately 12 weeks to first flowering from planting a rooted cutting.

*Growth habit.*—Compact, low growing and upright.

*Branching habit.*—Lateral branching is encouraged by pinching or stopping the stem at 5-8 cm above the growing surface.

*Suggested container size.*—1-gallon container.

*Use.*—Ornamental for use as a landscape plant or container plant.

*Type.*—Herbaceous perennial.

*Height of plant.*—45 cm-50 cm.

*Width of plant.*—40 cm.

*Cultural requirements.*—Grow in full sun with moderate water, avoiding drying out or saturation.

*Resistance or susceptibility to diseases and pests.*—In common with all plants of the genus, 'Fanfare Serenade' is susceptible to bacterial pathogens associated with overwatering, and to feeding by thrips (*Thysanoptera*) and aphids (*Aphididae*).

*Hardiness.*—Survives in USDA Hardiness Zone 6 (not tested in colder zones).

*Flowering period.*—From late April or early May until September or October.

Stem:

*Stem description.*—Single stem below point of initial pruning or stopping. Branches then develop from the base of the stem and from the point of pruning.

*Stem shape.*—Terete.

*Stem dimensions.*—2 cm in length (plants were pruned or stopped at this height), 6 mm. in diameter at soil level.

*Stem internode length.*—15 mm-20 mm.

*Stem color.*—145C.

*Stem surface.*—Pubescent, hairs fine, 2 mm in length, color white NN155D.

Branches:

*Branch description.*—Primary branches arise from the base and from the first node at which the plants were initially pruned. Secondary branches arise without further pruning as the primary branches begin to flower. All branches bear a terminal inflorescence.

*Branch shape.*—Terete.

*Branch quantity.*—5-6 primary branches, 10-14 secondary branches.

*Branch dimensions.*—Primary branches 30-35 cm in length (to base of peduncle of terminal inflorescence), 3-4 mm in diameter. Secondary branches 25 cm-35 cm in length, 3 mm in diameter.

*Branch internode length.*—1.5 mm-3.0 mm.

*Branch color.*—145C.

*Branch surface.*—Pubescent, hairs fine 1-2 mm in length, color white NN155D.

Foliage:

*Type.*—Evergreen.

*Leaf arrangement.*—Alternate.

*Leaf form.*—Simple.

*Leaf quantity.*—8-10 leaves per primary stem, 4-5 leaves per secondary stem.

*Leaf shape.*—Oblanceolate and asymmetrically lobed, 3-4 lobes on each edge.

*Leaf aspect.*—Upward facing.
*Leaf length.*—10.5 cm.
*Leaf width.*—4.2 cm in width.
*Leaf color* (*both surfaces*).—143C.
*Margin.*—Entire, smooth, glabrous.
*Leaf apex.*—Rounded.
*Leaf base.*—Cordate.
*Leaf venation pattern.*—Pinnate.
*Veins.*—All veins raised on abaxial surface, midrib raised on adaxial surface. Vein color: (both surfaces), 145C.
*Leaf surface* (*both surfaces*).—Pubescent, fine hairs 2.5 mm-3.5 mm in length, color NN155D.
*Leaf attachment.*—Sessile.

Inflorescence:
*Inflorescence type.*—Capitulum.
*Inflorescence shape.*—Radiate with center disc.
*Inflorescence aspect.*—Facing upward.
*Dimensions of inflorescence.*—80 mm in diameter and 25 mm in height.
*Number of inflorescences per plant.*—Approximately 18-25 inflorescences in colored bud and flower at one time.
*Blooming season.*—Spring, summer and fall.
*Peduncle shape.*—Cylindrical, light longitudinal raised ribs, 5-6 ribs per circumference.
*Peduncle dimensions* (*above uppermost leaf*).—Up to 12.5 cm in length, 3.5 mm in diameter.
*Peduncle surface.*—Pubescent, fine hairs up to 3.5 mm in length, hair color N155D.
*Peduncle color.*—138A between longitudinal ribs, ribs 145B. Anthocyanin coloration present in streaks, color N79C.
*Peduncle strength.*—Strong and stiff.

Bud:
*Shape.*—Rotate whorl.
*Dimensions* (*immediately prior to cracking color*).—12 mm in diameter, 10 mm in depth.
*Color.*—138B.

Ray florets:
*Ray floret shape.*—Funnelform.
*Ray floret surface* (*both surfaces*).—Smooth, glabrous.
*Ray floret arrangement.*—Radiate.
*Ray floret aspect.*—Initially strongly upward-facing, then slightly above the horizontal when newly fully open, then horizontal and drooping as ray florets age and fade.
*Number of ray florets per inflorescence.*—20-22.
*Fused or unfused.*—Ray florets are partially longitudinally fused to form corolla tube.
*Margins of ray florets.*—Entire.
*Veins of ray florets.*—Fine parallel and branched longitudinal veins, color N79B, prominent on outer ray floret surface, fainter on inner ray floret surface.
*Ray floret dimensions* (*overall, from base of corolla tube to apex*).—37 mm in length, 17 mm in width measured at ray floret apex.
*Ray floret lastingness.*—Ray florets remain fresh and bright for 7-10 days and are self-cleaning thereafter.
*Corolla tube dimensions* (*ray florets fused*).—11 mm in length, 2 mm in diameter at tube base.
*Corolla tube color* (*outer surface*).—N34A.
*Corolla tube color* (*inner surface*).—43A.
*Ray floret color* (*both surfaces, excluding yellow apices*).—43A.
*Ray floret apices* (*both surfaces*).—17C coloration extends 3 mm-5 mm inward from ray floret apex.

Disc Florets:
*Disc description.*—Closely-packed disc florets initially in flat plane, becoming domed then hemispherical as disc florets expand and age.
*Quantity of disc florets per inflorescence.*—100-120.
*Disc floret description.*—Tubular corolla tube with short free and flared apical section.
*Disc floret dimensions.*—13 mm in length and 3 mm in diameter (apex).
*Disc floret corolla tube.*—8 mm in length.
*Disc floret tube color.*—185B.
*Disc florets unfused portion* (*both surfaces*).—45A.
*Chaff* (*surrounds disc floret corolla tube*).—Translucent, paper-like, 6 mm in length, bearing 3 or 4 hair-like spurs, 3-4 mm in length.
*Chaff color, including spurs.*—155A.

Involucral bracts:
*Involucral bracts arrangement.*—2-3 whorls of involucral bracts.
*Involucral bract quantity.*—Approximately 25, of which approximately 8 large bracts in lowest whorl and 15-20 small bracts in upper whorls.
*Shape of involucral bract.*—Oblanceolate.
*Involucral bract dimensions* (*lowest whorl*).—14 mm in length, 6 mm in width.
*Involucral bract dimensions* (*upper whorls*).—10 mm in length, 3.5 mm in width.
*Involucral bract margin.*—Entire.
*Involucral bract apex.*—Acute.
*Involucral bract base.*—Truncate.
*Involucral bract color* (*both surfaces*).—143B.
*Involucral bract surface* (*both surfaces*).—Puberulent.

Reproductive organs:
*Stamens.*—Present on disc florets only. Stamen quantity: 5 per disc floret. Filament dimensions: 3 mm in length, less than 0.5 mm in diameter. Filament color: 187B. Anther shape: Ellipsoidal. Anther dimensions: Approximately 3 mm in length, 1.5 mm in diameter. Anther color: 166A. Pollen amount: Light. Pollen color: 17A.
*Pistil.*—Present on disc florets only. Pistil quantity: 1 per disc floret. Style dimensions: 10 mm-12 mm in length, 2 mm in diameter. Style color: 166B. Stigma shape: short, plumose Stigma dimensions: 3 mm in length, 2 mm in diameter. Stigma color: 166B. Ovary (observed immature only): Position, inferior; shape, globose; color 150C. Seed: None found to date.

I claim:

1. A new and distinct cultivar of *Gaillardia* Plant Named 'Fanfare Serenade' as described and illustrated herein.

* * * * *